United States Patent [19]
Luthe et al.

[11] Patent Number: 5,977,440
[45] Date of Patent: Nov. 2, 1999

[54] DNA MOLECULE ENCODING A 33KD CYSTEINE PROTEINASE AND ITS USE IN TRANSFORMING PLANTS TO PROVIDE INSECT RESISTANCE

[76] Inventors: Dawn S. Luthe, 402 Dorman; W. P. Williams, 344 Dorman, both of Mississippi State, Miss. 39762; Binghua Jiang, 600 N. Wolfe St., Baltimore, Md. 21873; Tibor Pechan, 412 Dorman, Mississippi State, Miss. 39762

[21] Appl. No.: 08/641,314

[22] Filed: Apr. 30, 1996

[51] Int. Cl.$^6$ .............................. C12N 15/29; C12N 15/82; A01H 4/00; A01H 5/00
[52] U.S. Cl. ..................... 800/298; 800/295; 536/24.1; 536/23.6; 435/419; 435/69.1; 435/320.1
[58] Field of Search ................................ 800/205, 250, 800/295, 298; 435/69.1, 172.3, 320.1, 419; 536/23.6, 24.1

Primary Examiner—Douglas W. Robinson
Assistant Examiner—Thomas Haas
Attorney, Agent, or Firm—Oblon, Spivak, McClelland, Maier & Neustadt, P.C.

[57] ABSTRACT

A cDNA molecule encoding for a particular 33 kD cysteine proteinase derived from maize is provided. When expressed in a plant, particularly corn or cotton, the protein provides insect resistance to the plant, and when expressed in the anther, the 33 kD cysteine proteinase provides sterility in the male of the plant species. The cDNA molecule can also be used as a probe to isolate suitable promoters for regulating expression of a 33 kD cysteine proteinase in callus or to provide a transformed baculovirus, which confers insect resistance upon a plant when the plant is infectted with the transformed baculovirus. Additionally, a DNA sequence of 264 base pairs in length is provided that provides enhanced enzymatic/catalytic activity in proteins expressed when the 264 base pair sequence is operably linked to a DNA molecule encoding for a cysteine proteinase.

13 Claims, 3 Drawing Sheets

```
          10        20        30        40        50        60
5'  GAATTCGGCACGAGGGCGGACGAGGAGGTGCGGCGCATGTACGAGGCGTGGAAGTCGAAG
     E  F  G  T  R  A  D  E  E  V  R  R  M  Y  E  A  W  K  S  K 70        80        90       100       110       120
    CACGGGCGCGGCGGCACGAGCAACGACGACTGCGACATGGCGCCGGCGATGATGAGCAGG
     H  G  R  G  G  T  S  N  D  D  C  D  M  A  P  A  M  M  S  R 130       140       150       160       170       180
    AGGAGGAGGACCGCCGGCTGCGCTGGAGGTGTTCCGCGACACCTTCGGTACATCGACGCG
     R  R  R  T  A  G  C  A  G  G  V  P  R  H  L  R  Y  I  D  A 190       200       210       220       230       240
    CACACGCGAGGCGACGCTGGGCTCCACACCTTCCGCCTCGGCCTCACCCCCTTCGCCGAC
     H  T  R  G  D  A  G  L  H  T  F  R  L  G  L  T  P  F  A  D 250       260       270       280       290       300
    CTCACCCTGGAGGAGTACCGTGGCCGCTTCCTCGGCTTTCGCGCCCGCGGCCGCGCAGCG
     L  T  L  E  E  Y  R  G  R  F  L  G  F  R  A  R  G  R  A  A 310       320       330       340       350       360
    GCCCGCTACGGCTCCGGCTACAGCGTCCGCGGCGGCGACCTCCCCGACGCCATCGACTGG
     A  R  Y  G  S  G  Y  S  V  R  G  G  D  L  P  D  A  I  D  W 370       380       390       400       410       420
    CGCCAGTTGGGCGCCGTCACCGAGGTCAAGGACCAGCAACAGTGCGGTGGGTGCTGGGCG
     R  Q  L  G  A  V  T  E  V  K  D  Q  Q  Q  C  G  G  C  W  A 430       440       450       460       470       480
    TTCTCGGCGGTGGCGGCCATCGAGGGGGTGAACGCGATCGCGACGGGTAACCTGGTGTCG
     F  S  A  V  A  A  I  E  G  V  N  A  I  A  T  G  N  L  V  S 490       500       510       520       530       540
    CTGTCGGAGCAGGAGATCATCGACTGCGACGCCCAGGACAGCGGCTGCGACGGCGGGCAG
     L  S  E  Q  E  I  I  D  C  D  A  Q  D  S  G  C  D  G  G  Q
```

*FIG. 1A*

```
       550        560        570        580        590        600
ATGGAGAACGCGTTCCGGTTCGTCATCGGCAACGGCGGGATCGACACCGAGGCCGACTAC
 M  E  N  A  F  R  F  V  I  G  N  G  G  I  D  T  E  A  D  Y 610        620        630        640        650        660
CCCTTCATCGGAACCGACGGCACTTGTGACGCCAGCAAGGAGAAGAACGAGAAGGTCGCC
 P  F  I  G  T  D  G  T  C  D  A  S  K  E  K  N  E  K  V  A 670        680        690        700        710        720
ACCATAGATGGGTTGGTGGAGGTGGCGAGCAACAACGAGACGGCGCTGCAGGAGGCGGTG
 T  I  D  G  L  V  E  V  A  S  N  N  E  T  A  L  Q  E  A  V 730        740        750        760        770        780
GCGATCCAGCCCGTCAGTGTCGCCATCGACGCAAGCGGGCGTGCGTTCCAGCACTACAGT
 A  I  Q  P  V  S  V  A  I  D  A  S  G  R  A  F  Q  H  Y  S 790        800        810        820        830        840
TCGGGCATCTTCAACGGGCCATGCGGGACGAGCCTGGACCACGGCGTCACGGCGGTGGGC
 S  G  I  F  N  G  P  C  G  T  S  L  D  H  G  V  T  A  V  G 850        860        870        880        890        900
TACGGCAGCGAGACGGCCAAGGACTACTGGATCGTGAAGAACTCGTGGAGGCCCAGCTGG
 Y  G  S  E  T  A  K  D  Y  W  I  V  K  N  S  W  R  P  S  W 910        920        930        940        950        960
GGCGAGGCCGGCTACATCCGCATGAGGCGCAACGTGCCCCGGCCCACGGGCAAGTGCGGC
 G  E  A  G  Y  I  R  M  R  R  N  V  P  R  P  T  G  K  C  G 970        980        990        1000       1010       1020
ATCGCCATGGACGCGTCCTACCCTGTGAAGGACACCTACCACCCCGGCACCGGCACCGCC
 I  A  M  D  A  S  Y  P  V  K  D  T  Y  H  P  G  T  G  T  A 1030       1040       1050       1060       1070       1080
ACGGCTAGGGCAGCTGCCATGGATGTGATCAAGATGGTTCTTGCTTAGGAGGGAGCGAGC
 T  A  R  A  A  A  M  D  V  I  K  M  V  L  A  *  E  G  A  S
```

*FIG. 1B*

```
          1090      1100      1110      1120      1130      1140
GGAGCAGGCAGCAGAGAGCCGAGGGTCTTGTCGTGTTGAACTTTACATAGGGTAGCTAGG
G  A  G  S  R  E  P  R  V  L  S  C  *  T  L  H  R  V  A  R 1150      1160      1170      1180      1190      1200
TACCACTGGGGATAATTAAGTTAATCCGTTATGGTGTGGCAAGTTAATTAATATGTGCGT
Y  H  W  G  *  L  S  *  S  V  M  V  W  Q  V  N  *  Y  V  R 1210      1220      1230      1240      1250      1260
ATCTCTTTTGATGAGTGGCATATATGATGTAATGAAGTTACATAAACTCAAATAAAGTCG
I  S  F  D  E  W  H  I  *  C  N  E  V  T  *  T  Q  I  K  S 1270      1280      1290
TAATCGTAATGGTAAAAAAAAAAAAAAAAAA  3'
*  S  *  W  *  K  K  K  K  K
```

DNA MOLECULE ENCODING A 33KD CYSTEINE PROTEINASE AND ITS USE IN TRANSFORMING PLANTS TO PROVIDE INSECT RESISTANCE

BACKGROUND OF THE INVENTION

1. Field of the Invention

The present invention relates to plant genetic engineering, particularly to a cDNA encoding a Maize 33 kD cysteine proteinase and its use to transform cells to express the cysteine proteinase to provide insect resistance.

2. Discussion of the Background

The larvae of both fall armyworm and southwestern corn borer are serious insect pests of corn (*Zea mays* L.) in the southern United States and cause damage to plants by feeding on leaves within the whorls. Several germplasm lines with resistance to these two insects have been developed and released (Williams et al, *Crop Sci.*, 22:1269–1270 (1982); Williams et al, *Crop Sci.*, 24:1217 (1984); Williams et al, *Crop Sci.*, 30:757 (1990)). These lines also show resistance to several additional lepidopterous insects, including the sugarcane borer (*Diatraea saccharalis* [Fab]), the corn earworm (*Helicoverpa zea* [Boddie]), and the European corn borer (*Ostrinia nubilalis* [Huber]) (Davis et al, *Miss. Agric. For. Exp. Stn. Tech. Bull.*, 157:1–6 (1988)).

Fall armyworm and southwestern corn borer larvae feed more extensively on whorls of susceptible plants than they do on resistant plants. Thus, larvae recovered from resistant plants are smaller than those recovered from susceptible plants (Williams et al, *Crop Sci.*, 29:913–915 (1989)), with both antibiosis and nonpreference appearing to be operative as mechanisms of resistance (Wiseman et al, *J. Econ. Entomol.*, 74:622–624 (1981) and Wiseman et al, *Protection Ecology*, 5:135–141 (1983)). Similar results have been obtained using callus initiated from mature embryos of resistant and susceptible genotypes (Williams et al, *Crop Sci.*, 23:1210–1212 (1983)). Attempts to identify specific secondary metabolites that may be involved in resistance have been inconclusive (Hedin et al, *J. Agric. Food Chem.*, 32:262–267 (1984)).

Several endogenous plant proteins may confer resistance to insect pests. These include the Ser proteinase inhibitors, lectins, and α-amylase inhibitors (Shade et al, *Biotechnology*, 12:793–796 (1994)). Proteins such as these may not be highly toxic, but they can control the rate of development of pest insect populations (Ibid.). These moderately toxic proteins exert a less stringent selection pressure than highly toxic insecticides and slow the development of resistance (Tabashnik, *Annu. Rev. Entomol.*, 39:47–49 (1994)).

Although there is little specific information about the role of proteinases in insect resistance, it is generally believed that hydrolytic enzymes are involved in the plant defense response (Boller, in "Plant Proteolytic Enzymes, Vol. I, M. J. Dalling, Ed., CRC Press, Boca Raton, Fla., (1986)). Typically, hydrolytic enzymes are sequestered in the vacuole and are released when it is broken. The released hydrolases may be the first line of defense against pathogen or herbivore attack (Ibid.). Some proteinases such as the one found in *Phaseolus vulgaris* leaves (Van der Wilden et al, *Plant Physiol.*, 73:576–578 (1983)) are present in the cell wall and thus provide another site of defense. Feeding by *Spodoptera littoralis* induces Leu aminopeptidase in tomato (Pautot et al, *Proc. Natl. Acad. Sci.* USA, 90:9906–9910 (1993)). This proteinase may be involved in systemic response to wounding, which leads to the expression of plant defense proteins (Pearce et al, *Science*, 253:895–897 (1991)).

Cysteine proteinases are endoproteinases found in bacteria, eukaryotic microorganisms, plants and animals (Barrett, in "Plant Proteolytic Enzymes, Vol. I, M. J. Dalling, Ed., CRC Press, Boca Raton, Fla., pp. 1–16 (1986)). One of the most studied cysteine proteinases is papain, which is found in the latex of *Carica papaya* L (Ibid.). There is a large family of enzymes with similarity to papain, including the cathepsins present in mammalian lysosomes (Ibid.). The thiol group on cys-25 of papain is required for activity, hence the name cysteine proteinase. This class of enzymes is inhibited by iodoacetate, E64, and small proteins called cystatins (Ibid.).

Many cysteine proteinases have been identified in plants. One group, synthesized during seed germination, is involved in storage protein degradation. Several isozymes from this group have been purified and cloned from barley (Kohler et al, *Plant Cell*, 2:769–783 (1990)), corn (deBarros et al, *Plant Science*, 99:189–197 (1994)) and Mitsuhashi et al, *Plant Physiol.*, 104:401–407 (1994)), rice (Watanabe et al, *J. Biol. Chem.*, 266:16897–16902 (1991)), and other species.

Although the nucleus of every cell contains the entire complement of genomic DNA, a cell in a given tissue does not express every single gene in the genome. Rather, a given cell expresses a population of genes which code for proteins that are critical for maintaining cellular physiology. The challenge every cell faces is to express thousands of different genes at exactly the right times and in exactly the right amounts to prevent cellular physiology from becoming compromised.

Tissue-specific gene expression is often regulated at the level of gene transcription. Transcription is the process by which double-stranded DNA is read into singlestranded RNA. The processes of transcription initiation, and regulation of subsequent changes in rates of transcription reinitiation, are controlled by protein-DNA interactions.

Transcription is a highly regulated process in which nuclear gene regulatory proteins (often called transcription factors) bind, with high affinity, to short (five to fifteen base pair) lengths of DNA sequence known as control elements. Protein-DNA interactions occur in the promoter, 5' flanking, and 3' flanking regions of the gene. Through such protein-DNA interactions, gene expression is programmed to respond to changes in extracellular signals such as light, temperature, growth factor concentration, hormone concentration, and drug concentration and post-translational modification of protein (level of phosphorylation, myristylation, etc.). Such transcriptional mechanisms regulate tissue-specific protein expression.

SUMMARY OF THE INVENTION

Accordingly, one object of this invention is to provide a cDNA that encodes a 33 kD cysteine proteinase capable of providing insect resistance to plants transformed with the cDNA.

Another object of the present invention is to provide a vector for use in transforming plants, particularly corn plants, that contains the cDNA encoding a 33 kD cysteine proteinase.

Another object of the present invention is to provide a transgenic plant that contains a vector comprising a DNA molecule encoding a 33 kD cysteine proteinase.

Another object of the present invention is to provide a method for the induction of male plant sterility by providing for the expression of a 33 kD cysteine proteinase in the anther of the plant, preferably a corn plant, thereby preventing formation of viable pollen.

Another object of the present invention is to provide a 264 base pair segment of DNA which when coupled to the 3' end of a second DNA sequence that encodes a cysteine proteinase, provides the resulting expressed protein with enhanced catalytic-enzymatic properties, particularly in activity and stability.

Another object of the present invention is to provide a method for providing insect resistance to plants by infecting the plants with a baculovirus that has been transformed by insertion of an expression vector containing the cDNA sequence of the Mir1 gene.

These and other objects of the present invention have been satisfied by the discovery of a cDNA molecule that encodes a 33 kD cysteine proteinase capable of providing insect resistance when expressed in a transformed cell or plant and having the nucleotide sequence of FIG. 1.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 1 shows the nucleotide sequence of the cDNA of the present invention and the amino acid sequence of the 33 kD cysteine proteinase encoded thereby.

DETAILED DESCRIPTION OF THE PREFERRED EMBODIMENTS

The present invention relates to a full-length cDNA clone that encodes a 33 kD cysteine proteinase that conveys insect resistance when expressed in plants or other cells. The cDNA of the present invention has been dubbed Mir1 and can be isolated from a maize callus cDNA library. Mir1 has the nucleotide sequence shown in FIG. 1.

To prepare the cDNA of the present invention, a cDNA library is prepared from callus initiated from mature embryos of the inbred Mp708 (as described in B. Jiang, "Relationship of a 33 kD Putative Cysteine Proteinase with Fall Armyworm Resistance in Corn," Ph.D. Thesis, Mississippi State University (1994), the content of which is hereby incorporated by reference). This inbred is resistant to feeding by fall armyworm and several other lepidopteran insects. Both Mp708 and Mp704 inbreds were jointly released by the USDA-ARS and the Mississippi Agricultural and Forestry Experiment Station. After their release, these germplasm lines were registered with the Crop Science Society of America. Notices of registration were published in Williams et al, *Crop Sci.*, 22:1269–1270 (1982) and Williams et al, *Crop Sci.*, 30:757 (1990), both of which are hereby incorporated by reference. These references provide information on the identity of the inbreds, their development and how to obtain seed of the particular lines.

Amplification of the cDNA sequence encoding the cysteine proteinase using the PCR, allows for expression of the PCR product in *E. coli*. The preferred promoter for expression in *E. coli* is the T7 promoter, described by Martens et al, *Bio/technology* 13:175–179 (1995), the relevant portions of which are hereby incorporated by reference. The expressed protein has the correct 33 kD molecular weight, immunoreacts with polyclonal antibody to authentic 33 kD protein, and has cysteine proteinase activity. Comparisons indicate that the N-terminal amino acid sequence of the 33 kD proteinase is approximately 50% homologous to the papain superfamily.

The synthesis of some cysteine proteinases (or their respective mRNA's) appears to be up-regulated by certain environmental stresses, phytohormones, or during senescence. Drought, salt stress, cold temperature, wounding, ethylene and ovary or flower senescence are known to induce the synthesis of putative cysteine proteinases in various plants. While the mechanism of expression in callus is not completely understood, since callus often emits large amounts of ethylene, the expression of the 33 kD cysteine proteinase in corn callus may be regulated by ethylene.

Callus containing the 33 kD cysteine proteinase retards the growth of fall armyworm larvae. The cDNA can be used to express large amounts of the 33 kD proteinase in various types of cells, including but not limited to bacteria, yeast, and baculovirus.

Using genetic engineering techniques, the cDNA encoding the 33 kD cysteine proteinase can be transferred to plant species susceptible to lepidopteran feeding, such as corn, cotton, sugarcane or sugar beets to provide larval growth inhibition upon expression. Preferably, the cDNA is transferred to callus from susceptible maize genotypes to provide these genotypes with larval growth inhibition.

The sequence of Mir1 has been found to have partial homology with several known nucleotides that encode other cysteine proteinases. One significant difference is found in a 264 base pair segment in the 3' region of the Mir1 gene. This difference is not a sequencing artifact since both Mir1 and the PCR fragment derived from it have the same sequence.

In an alternative embodiment of the present invention, this 264 base pair sequence in the 3' terminus of the Mir1 gene (nucleotide position 987 to position 1250) can be coupled to the 3' end of other cDNA's encoding cysteine proteinases in order to enhance their enzymatic activity and catalytic turnover. Suitable other cDNAs that can be coupled to this 264 base pair sequence include the cDNAs encoding other cysteine proteinases found in various plants and animals, including other cysteine proteinases derived from corn.

Mapping of the Mir1 clone shows that Mir1 maps to a single locus on chromosome 6 near the RLFP locus umc59 on the U.S. Department of Agriculture's Immortal $F_2$ mapping population CO159×Tx303. Using quantitative trait locus analysis, Mir1 exhibits large significant effects for maysin concentration in maize and for larval growth inhibition. The dominant gene action and lack of epistasis with other loci should make Mir1 easier to work with than other genes of similar activity.

In a further embodiment of the present invention, an expression vector is provided for use in transforming plants, preferably corn or cotton plants, most preferably corn plants, and promoting the expression of the 33 kD cysteine proteinase in the transformed plant. The vector comprises the Mir1 cDNA sequence of the present invention operably linked to one or more control elements. Particular control elements include: promoters, termination sequences, and various markers. A preferred promoter is the ubiquitin promoter, described by Christensen et al, *Plant Mol. Biol.*, 18:675–689 (1992), the relevant portions of which are hereby incorporated by reference. The transformation vector, pAHC25, which has both gus (β-glucuronidase) and bar (resistance to phosphinothricin, the herbicides Bialophos/Basta/Ignite) each regulated by the ubiquitin promoter and ubi1 intron (Ibid.) is preferred. The transformation vector can be constructed by removing the region of pAHC25 encoding gus with SmaI and SacI. The full length cDNA clone of Mir1 can be excised from pBluescript using SmaI and HincII and blunt end ligated into pAHC25 under the regulation of the ubiquitin promoter. The correct orientation of Mir1 can be determined by restriction mapping. Within the context of the present invention, the term "operably linked" means that the nucleotide sequence is linked so as to promote expression of the cDNA of the present invention.

Plants can be transformed with the cDNA of the present invention by use of a suitable expression vector containing that cDNA and conventional methods for transforming plants, preferably plants susceptible to lepidopteran feeding, most preferably corn plants.

A suitable method for the generation of an expression vector for transforming corn plants is described in Boston et al, U.S. Pat. No. 5,332,808, the relevant portions of which are hereby incorporated by reference. In addition, any other conventional method for preparing an expression vector can be used to provide the expression vector of the present invention.

A further embodiment of the present invention relates to a transgenic corn plant or seed that contains the vector of the present invention comprising the Mir1 cDNA sequence. The transformation of corn plants can be effected using conventional techniques as described in Boston et al, U.S. Pat. No. 5,332,808, already incorporated by reference above or as described in Armstrong et al, Crop Science, 35(2):550–557 (1995), the relevant portions of which are hereby incorporated by reference.

Germination of the transformed corn plant cell or seed into a corn plant can be performed in accordance with techniques well known in the art for planting and growing plants.

The preparation of suitable expression vectors for corn has been described above. Expression vectors for other plants susceptible to lepidopteran feeding can be prepared using conventional procedures and known promoters. For example, to transform cotton fiber cells and ultimately produce a transgenic cotton plant, the methods described in Umbeck et al, U.S. Pat. Nos. 5,004,863 and 5,159,135 can be used, by substituting in the cDNA sequence of the present invention into the vector as the active sequence to be transferred to the cotton. These patents describe the production of suitable vectors for transforming cotton, the selection of the thus transformed cotton fiber cells and germination of the transformed cotton fiber cell into a cotton fiber plant. These patents are hereby incorporated by reference.

The 33 kD cysteine proteinase encoded by the Mir1 molecule provides the corn plant, in which it is expressed, with insect resistance being provided through at least one mechanism of inhibition of larval growth, resulting in reduced larval weight and inability to mature properly.

In an additional embodiment, the cDNA may be used in a method for targetted expression in the anther of the plant. By expressing the 33 kD cysteine proteinase in the anther of the plant, the male of the plant species is rendered sterile, and does not produce viable pollen. In preparing the anther specific expression vector, it is preferred to use the TA29-anther specific promoter disclosed by Mariani et al, Nature 347:737–741 (1992)).

In still another embodiment, the Mir1 gene may be inserted into a baculovirus using an expression vector containing the Mir1 gene and the resulting transformed baculovirus used to infect a plant in need of insect resistance. The transformed baculovirus then expresses the 33 kD cysteine proteinase and confers insect resistance properties on the infected plant. The transformed baculovirus can be produced using known methods as described in Korth et al, Proc. Natl. Acad. Sci. USA, 90: 3388–3392 (1993), Tomalski et al, Nature, 352: 82–85 (1991) and Stewart et al, Nature, 352: 85–88 (1991), the relevant portions of which are incorporated herein by reference.

In another alternative embodiment, the Mir1 gene can be used as a probe to identify a promotor (regulatory sequence) that regulates the expression of the 33 kD cysteine proteinase in callus. In performing this embodiment, a genomic clone encoding Mir1 is isolated by using Mir1 to screen a genomic library from Mp704 or Mp708 in accordance with the procedures described in Sambrook et al, Molecular Cloning, Ed. 2 (1989). Positive clones are sequenced to identify consensus promoter regions in the 5' region of the gene by data base comparison. Alternatively, inverse PCR can be used to isolate the 5' region of the gene, as described by Ochman et al, Nucl. Acid. Res., 19:3055–3056 (1988) and Trigilia et al, Nucl. Acid. Res., 16:8186 (1988), the relevant portions of which are hereby incorporated by reference. The identified regulatory regions can be confirmed by fusion to an E. coli GUS (β-glucuronidase) reporter gene system and transferred to corn using particle bombardment as described by Christensen et al.

Having generally described this invention, a further understanding can be obtained by reference to certain specific examples which are provided herein for purposes of illustration only and are not intended to be limiting unless otherwise specified.

EXAMPLES

Isolation of poly(A)$^+$-RNA from callus of the resistant maize inbred Mp708 and cDNA library construction were done as previously described (Jiang, Ph.D. Thesis, Mississippi State University, 1994). The library was screened using the following degenerate oligonucleotides derived from the N-terminal amino acid sequence of the 33 kD protein: oligo#34745-001 (GAGGACAAGCNGAYGC) and oligo#34745-002 9GTSGACGACCARCRGC). The clone Mir1 was isolated using this screening protocol.

The 1 kB PCR fragment derived from Mir1 was cloned into the expression vector pQE9 under the regulation of the T7 promoter (Martens et al, Bio/technology, 13:175–179 (1995)). Transformation of E. coli XL1 blue and induction with thiogalactopyranoside resulted in the expression of the 33 kD cysteine proteinase in the bacterial inclusion bodies. Extraction of the inclusion bodies with urea and guanidine, chromatography over nickel resin and careful dialysis to remove urea and guanidine resulted in purified 33 kD protein with activity nearly equivalent to that purified from callus (Dolinar et al, Biol. Chem., 376:385–388 (1995)).

Three pieces of evidence suggest that the presence of the 33 kD proteinase, or one of its metabolic products, inhibits the growth of larvae reared on the callus. First, analysis of callus lines from $F_2$ progeny of Mp704×Tx601 indicated that the concentration of the 33 kD proteinase and the weight of the fall armyworm larvae reared on the callus were negatively correlated. Second, when the callus of Mp704 changed from nonfriable to friable, it no longer retarded insect growth, and the 33 kD proteinase was absent. Third, the 33 kD cysteine proteinase isolated from the resistant inbred was 7-fold more active than the 36 kD cysteine proteinase isolated from the susceptible (Ab24E) inbred. These results suggest that the presence of a 33 kD protein with a relatively high cysteine proteinase activity may be required to inhibit larval growth in callus. While the exact mechanism of insect resistance from the cysteine proteinase is not known, it is believed to operate by two possible pathways: (1) Ingestion of the cysteine proteinase could directly harm the larvae, or (2) it could catalyze a reaction leading to a toxic substance. In addition to these possibilities, there are specific cysteine proteinases involved in apopotosis (programmed cell death) in many organisms (Steller, *Science,* 267:1445–1449 (1995)).

Mapping Results

In a quantitative trait locus analysis of the maize population (GE37×FF8)$F_{2:3}$, maysin concentration of silks grown in Missouri and Georgia, and weight of corn earworm larvae grown on artificial diets containing silks of the progeny lines were investigated. Maysin is a flavonoid compound that inhibits earworm growth. Corn earworm is another lepidopteran species. Growth of corn earworm larvae is inhibited when they are reared on resistant corn genotypes such as Mp704 and Mp708 (Davis et al (1988)). Using single-factor analysis of variance, all traits were significantly associated (p<0.001) with umc59, a marker near Mir1. That marker explained 11.5, 9.1, and 5.6% of the phenotypic variance for larval weight, maysin (Missouri), and maysin (Georgia), respectively. Using another type of analysis, interval mapping with MapMaker/QTL software, peak significance levels occurred very close to umc59 for larval wieght and maysin (Missouri), but the significance was below the threshold level for maysin (Georgia). The umc59 region explained 12.3% of the phenotypic variance for larval weight and 9.4% for maysin (Missouri). Based on comparison of genotype means at umc59, gene action appears to be largely dominant for low larval weight and high maysin. None of the epistatic interactions of umc59 with other markers was significant at p<0.01. Thus relatively large, significant effects were found in the Mir1 region for maysin concentration and larval growth inhibition. Dominant gene action in the desired direction and lack of epistasis with other loci make the gene(s) in this region easier for breeders to work with.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An isolated DNA molecule having the nucleotide sequence of SEQ ID NO 1.

2. An expression vector comprising a DNA molecule having the nucleotide sequence of SEQ ID NO 1 operably linked to one or more control elements.

3. A plant seed capable of germination into a plant containing the vector of claim 2, wherein the seed has been stably transformed with the vector.

4. A plant germinated from the seed of claim 3.

5. A method for providing insect resistance to a plant species susceptible to leptidopteran feeding, comprising:

(a) introducing into a plant seed, from a plant species susceptible to leptidopteran feeding, a vector comprising a 264 base pair DNA molecule having a nucleotide sequence of from position 987 to position 1250 of the Mir1 gene in SEQ ID NO 1 operably linked to a cDNA encoding for a cysteine proteinase and one or more control elements; and (b) germinating the plant seed into a plant.

6. The method of claim 5, wherein said 264 base pair DNA molecule and said cDNA encoding for a cysteine proteinase combined form the entire sequence of the Mir1 gene in SEQ ID NO 1.

7. The method of claim 5, wherein said plant species susceptible to lepidopteran feeding is a member selected from the group consisting of corn, cotton, sugarcane and sugar beets.

8. The method of claim 6, wherein said plant species susceptible to lepidopteran feeding is a corn plant.

9. The method of claim 7, wherein said plant species susceptible to lepidopteran feeding is a corn plant.

10. A method for imparting sterility to a male member of a plant species, comprising:

(a) transforming an anther of the plant species by insertion of an expression vector comprising a DNA molecule having the entire nucleotide sequence of Mir1 from SEQ ID NO 1 operably linked to one or more control elements; and (b) expressing a 33 kD cysteine proteinase encoded by said DNA molecule in the anther of the plant species.

11. The method of claim 10, wherein said plant species is corn.

12. A DNA molecule consisting essentially of a DNA sequence of from position 987 to position 1250 of the Mir1 gene of SEQ ID NO 1.

13. A method for providing insect resistance to a plant in need thereof, comprising:

infecting said plant with a transformed baculovirus, wherein the transformed baculovirus has been transformed by insertion of an expression vector comprising a DNA molecule having a sequence of the Mir1 gene of SEQ ID NO 1 operably linked to one or more control elements such that said baculovirus expresses a 33 kD cysteine proteinase.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 1301 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GAATTCGGCA CGAGGGCGGA CGAGGAGGTG CGGCGCATGT ACGAGGCGTG GAAGTCGAAG        60

CACGGGCGCG GCGGCAGCAG CAACGACGAG TGCGACATGG CGCCCGGCGA TGATGAGCAG       120

GAGGAGGAGG ACCGCCGGCT GCGGCTGGAG GTGTTCCGCG ACAACCTTCG GTACATCGAC       180

GCGCACAACG CGGAGGCGGA CGCTGGGCTC CACACCTTCC GCCTCGGCCT CACCCCCTTC       240

GCCGACCTCA CCCTGGAGGA GTACCGTGGC CGCTTCCTCG GCTTTCGCGC CCGCGGCCGC       300

CGCAGCGGCG CCCGCTACGG CTCCGGCTAC AGCGTCCGCG GCGGCGACCT CCCCGACGCC       360

ATCGACTGGC GCCAGTTGGG CGCCGTCACC GAGGTCAAGG ACCAGCAACA GTGCGGTGGG       420

TGCTGGGCGT TCTCGGCGGT GGCGGCCATC GAGGGGGTGA ACGCGATCGC GACGGGTAAC       480

CTGGTGTCGC TGTCGGAGCA GGAGATCATC GACTGCGACG CCCAGGACAG CGGCTGCGAC       540

GGCGGGCAGA TGGAGAACGC GTTCCGGTTC GTCATCGGCA ACGGCGGGAT CGACACCGAG       600

GCCGACTACC CCTTCATCGG AACCGACGGC ACTTGTGACG CCAGCAAGGA GAAGAACGAG       660

AAGGTCGCCA CCATAGATGG GTTGGTGGAG GTGGCGAGCA ACAACGAGAC GGCGCTGCAG       720

GAGGCGGTGG CGATCCAGCC CGTCAGTGTC GCCATCGACG CAAGCGGGCG TGCGTTCCAG       780

CACTACAGTT CGGGCATCTT CAACGGGCCA TGCGGGACGA GCCTGGACCA CGGCGTCACG       840

GCGGTGGGCT ACGGCAGCGA GAGCGGCAAG GACTACTGGA TCGTGAAGAA CTCGTGGAGC       900

GCCAGCTGGG GCGAGGCCGG CTACATCCGC ATGAGGCGCA ACGTGCCCCG GCCCACGGGC       960

AAGTGCGGCA TCGCCATGGA CGCGTCCTAC CCTGTGAAGG ACACCTACCA CCCCGGCACC      1020
```

-continued

```
GGCACCGCCA CGGCTAGGGC AGCTGCCATG GGATGTGATC AAGATGGTTC TTGCTTAGGA      1080

GGGAGCGAGC GGAGCAGGCA GCAGAGAGCC GAGGGTCTTG TCGTGTTGAA CTTTACATAG      1140

GGTAGCTAGG TACCACTGGG GATAATTAAG TTAATCCGTT ATGGTGTGGC AAGTTAATTA      1200

ATATGTGCGT ATCTCTTTTG ATGAGTGGCA TATATGATGT AATGAAGTTA CATAAACTCA      1260

AATAAAGTCG TAATCGTAAT GGTAAAAAAA AAAAAAAAA A                          1301
```

(2) INFORMATION FOR SEQ ID NO:2:

(i) SEQUENCE CHARACTERISTICS:
        (A) LENGTH: 355 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Glu Phe Gly Thr Arg Ala Asp Glu Val Arg Arg Met Tyr Glu Ala
 1               5                  10                  15

Trp Lys Ser Lys His Gly Arg Gly Thr Ser Asn Asp Asp Cys Asp
                20                  25                  30

Met Ala Pro Ala Met Met Ser Arg Arg Arg Thr Ala Gly Cys Ala
            35                  40                  45

Gly Gly Val Pro Arg His Leu Arg Tyr Ile Asp Ala His Thr Arg Gly
     50                  55                      60

Asp Ala Gly Leu His Thr Phe Arg Leu Gly Leu Thr Pro Phe Ala Asp
65                  70                  75                  80

Leu Thr Leu Glu Glu Tyr Arg Gly Arg Phe Leu Gly Phe Arg Ala Arg
                85                  90                  95

Gly Arg Ala Ala Ala Arg Tyr Gly Ser Gly Tyr Ser Val Arg Gly Gly
            100                 105                 110

Asp Leu Pro Asp Ala Ile Asp Trp Arg Gln Leu Gly Ala Val Thr Glu
        115                 120                 125

Val Lys Asp Gln Gln Gln Cys Gly Gly Cys Trp Ala Phe Ser Ala Val
130                 135                 140

Ala Ala Ile Glu Gly Val Asn Ala Ile Ala Thr Gly Asn Leu Val Ser
145                 150                 155                 160

Leu Ser Glu Gln Glu Ile Ile Asp Cys Asp Ala Gln Asp Ser Gly Cys
                165                 170                 175

Asp Gly Gly Gln Met Glu Asn Ala Phe Arg Phe Val Ile Gly Asn Gly
            180                 185                 190

Gly Ile Asp Thr Glu Ala Asp Tyr Pro Phe Ile Gly Thr Asp Gly Thr
        195                 200                 205

Cys Asp Ala Ser Lys Glu Lys Asn Glu Lys Val Ala Thr Ile Asp Gly
210                 215                 220

Leu Val Glu Val Ala Ser Asn Asn Glu Thr Ala Leu Gln Glu Ala Val
225                 230                 235                 240

Ala Ile Gln Pro Val Ser Val Ala Ile Asp Ala Ser Gly Arg Ala Phe
                245                 250                 255

Gln His Tyr Ser Ser Gly Ile Phe Asn Gly Pro Cys Gly Thr Ser Leu
            260                 265                 270

Asp His Gly Val Thr Ala Val Gly Tyr Gly Ser Glu Thr Ala Lys Asp
        275                 280                 285

Tyr Trp Ile Val Lys Asn Ser Trp Arg Pro Ser Trp Gly Glu Ala Gly
290                 295                 300
```

```
Tyr Ile Arg Met Arg Arg Asn Val Pro Arg Pro Thr Gly Lys Cys Gly
305                 310                 315                 320

Ile Ala Met Asp Ala Ser Tyr Pro Val Lys Asp Thr Tyr His Pro Gly
            325                 330                 335

Thr Gly Thr Ala Thr Ala Arg Ala Ala Ala Met Asp Val Ile Lys Met
            340                 345                 350

Val Leu Ala
    355
```

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

GAGGACAAGN GAYGC                                      15

(2) INFORMATION FOR SEQ ID NO:4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

GTSGACGACC ARCRGC                                     16

(2) INFORMATION FOR SEQ ID NO:5:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Glu Gly Ala Ser Gly Ala Gly Ser Arg Glu Pro Arg Val Leu Ser Cys
1               5                   10                  15
```

(2) INFORMATION FOR SEQ ID NO:6:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Thr Leu His Arg Val Ala Arg Tyr His Trp Gly
1               5                   10
```

(2) INFORMATION FOR SEQ ID NO:7:

(i) SEQUENCE CHARACTERISTICS:
        (A) LENGTH: 8 amino acids

-continued (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Ser Val Met Val Trp Gln Val Asn
1               5

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Tyr Val Arg Ile Ser Phe Asp Glu Trp His Ile
1               5                   10

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Cys Asn Glu Val Thr
1               5

(2) INFORMATION FOR SEQ ID NO:10:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Thr Gln Ile Lys Ser
1               5

(2) INFORMATION FOR SEQ ID NO:11:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Lys Lys Lys Lys Lys
1               5